United States Patent [19]
Beck

[11] Patent Number: 5,645,527
[45] Date of Patent: Jul. 8, 1997

[54] HYDRATION ASSEMBLY FOR HYDRATING A BIOELECTRODE ELEMENT

[75] Inventor: Jon E. Beck, Salt Lake City, Utah

[73] Assignee: IOMED, Inc., Salt Lake City, Utah

[21] Appl. No.: 599,129

[22] Filed: Feb. 9, 1996

[51] Int. Cl.[6] .............. A61N 1/30; A61B 17/06; B65D 35/24
[52] U.S. Cl. .............. 604/20; 607/153; 222/93; 222/107; 206/438
[58] Field of Search .............. 604/20, 89–90, 604/289, 304–7, 416; 607/2–3, 153; 206/528, 440, 438, 505; 222/107, 92–3

[56] References Cited

U.S. PATENT DOCUMENTS

| | | |
|---|---|---|
| 2,702,146 | 2/1955 | Land . |
| 3,754,700 | 8/1973 | Bonk . |
| 4,072,249 | 2/1978 | Ekenstam et al. ............ 222/107 |
| 4,342,395 | 8/1982 | Brown ............ 206/528 |
| 4,383,529 | 5/1983 | Webster . |
| 4,941,574 | 7/1990 | Meehan . |
| 5,232,438 | 8/1993 | Theeuwes et al. ............ 604/20 |
| 5,236,412 | 8/1993 | Lloyd et al. . |
| 5,281,287 | 1/1994 | Lloyd et al. . |
| 5,288,289 | 2/1994 | Haak et al. ............ 604/20 |
| 5,310,404 | 5/1994 | Gyory et al. ............ 604/20 |

FOREIGN PATENT DOCUMENTS

| | | |
|---|---|---|
| 2066208 | 7/1981 | United Kingdom . |
| WO93/24177 | 12/1993 | WIPO ............ 604/20 |

Primary Examiner—Mark Bockelman
Assistant Examiner—Ellen Tao
Attorney, Agent, or Firm—Workman, Nydegger & Seeley

[57] ABSTRACT

The present invention provides methods and apparatus permitting rapid and thorough hydration of an initially dry hydratable matrix element contained within a bioelectrode element for use in an iontophoretic delivery device. The apparatus of the invention comprises a bioelectrode element for iontophoretic delivery of medicaments having at least one hydratable matrix element and associated removable hydration assembly. The removable hydration assembly includes an initially sealed liquid-storage component which maintains the desired hydrating liquid in isolation from the hydratable matrix element until such time as hydration is desired. At that time, the removable hydration assembly can be activated by the user through application of force to a pocket in a side of the sealed liquid-storage component to cause the pocket to become inverted and substantially aligned within an opposing pocket in the other side such that the sealed liquid-storage component unseals at a predetermined release location. The hydrating liquid is then released into the hydratable matrix element. Following hydration of the matrix element, the spent hydration assembly can be separated from the now-hydrated bioelectrode element.

29 Claims, 2 Drawing Sheets

HYDRATION ASSEMBLY FOR HYDRATING A BIOELECTRODE ELEMENT

BACKGROUND OF THE INVENTION

1. Technical Field

This invention relates to iontophoretic delivery devices used to deliver ions through the skin or other tissues. In particular, this invention relates to methods and apparatus for hydrating a hydratable bioelectrode element of an iontophoretic delivery device.

2. Background Information

Iontophoretic delivery of medicaments has been found useful in a number of different applications including, for example, delivery of pilocarpine salts as a diagnostic test for cystic fibrosis and delivery of lidocaine hydrochloride to anesthetize a localized area prior to some minor surgical procedure such as wart removal.

Typically, systems for iontophoretic delivery of medicaments use two bioelectrodes, one positive and one negative, each placed in electrical contact with a portion of the skin or a mucosal surface of the body. Also typical is that each bioelectrode contains an electrolyte solution and at least one of the electrolyte solutions contains an ionized medicament. An electrical power source, such as a battery, is connected to the electrodes to complete the electrical circuit through the body. The charge of the ionized solution determines bioelectrode polarity such that, when current is supplied, the medicament ions migrate away from the electrode and are thereby delivered through the skin or other tissue.

Some type of enclosure or other fluid-holding means is typically used to contain the ionized electrolyte or medicament solution such that a solution-receiving mechanism or structure on the enclosure is necessary to permit the introduction of solution thereinto. Such structure has typically included some type of orifice through which a hypodermic needle or syringe cannula may be inserted to allow delivery of the solution through the orifice into the interior of the enclosure. The use of such a solution-receiving mechanism increases the cost of the bioelectrode system and gives rise to potential spillage and leakage of solution. Such spillage and leakage can result in an inoperative or defective device.

More recent bioelectrode systems have used hydrophilic polymers to form means for holding the medicament and electrolyte solutions. See, for example, the preformed gel body described in U.S. Pat. No. 4,383,529 issued to Webster, incorporated herein by reference. Although such prehydrated gel bodies may prevent leakage and spillage problems, there may still be stability and storage problems. To address these problems, bioelectrodes containing initially "dry," i.e., non-hydrated, but hydratable, holding means for the medicament and electrolyte solutions have been developed. See, for example, the hydratable layers; of hydrogel sheets described in Lloyd et al., U.S. Pat. No. 5,236,412, incorporated herein by reference.

In addition, efforts have been directed to developing bioelectrode systems containing initially dry, but hydratable, solution-holding components wherein the means for hydrating the components is also self-contained. Thus, for example, Haak et al., U.S. Pat. No. 5,288,289 and Gyory et al., published international patent application, WO 93/24177, both of which are incorporated herein by reference, disclose various self-contained means for releasing hydrating liquid from liquid-storage components and thereby hydrating the initially dry solution-holding components.

In certain embodiments of the Haak patent, the hydrating liquid-storage components comprise breakable capsules filled with the desired hydrating liquid which are positioned within a layer of material such that the liquid is isolated from the hydratable solution-holding components. Squeezing or distorting of the hydrating liquid-storage component breaks the capsules and releases the hydrating liquid. The hydrating liquid flows onto the electrical current distribution element and through preformed passageways to the hydratable solution-holding component. Optional wicking material is described to enhance rapid transfer of the liquid across the electrode conductor surface where the liquid can flow through the passageways to the hydratable solution-holding component.

It can be seen that the hydrating rate, the completeness of the fluid transfer, and the fluid distribution pattern is affected by the characteristics and properties of the separate elements which must be in fluid communication, i.e., the interposed electrical current distribution element material, the hydrating liquid-storage component material, the hydratable solution-holding component material, and the optional wicking material. Other variables include the size, shape, and other characteristics of the flowthrough openings between the hydrating liquid-storage component and the hydratable solution-holding component, the distributional arrangement of the capsules within the hydrating liquid-storage component material, and even whether or not all of the capsules break or whether the encapsulized liquid is completely dispensed from the broken capsules. Moreover, inadvertent squeezing or distorting of the hydrating liquid-storage component could occur during manufacture, shipping, storing or handling of the device. Such an occurrence could break some or all of the hydrating liquid-filled capsules and cause premature hydration of the hydratable solution-holding component. Such premature hydration could result in an unusable or defective device.

Alternatively, the bioelectrode system disclosed in the Haak patent comprises separate components such that the hydrating liquid-storage component is covered by a removable liquid-impermeable sheet such that removal of the sheet exposes the hydrating liquid. The hydrating liquid-storage component is attached to one portion of the system. The hydratable solution-holding component is attached to a separate portion of the system. A user of the system removes the liquid-impermeable sheet to expose the hydrating liquid and then manually assembles the separate portions such that the hydrating fluid contacts, and thereby hydrates, the hydratable solution-holding component.

Alternatively, the system portions are not separate from each other but, rather, the portion attached to the hydrating liquid-storage component is positioned adjacent to the portion attached to the hydratable solution-holding component such that a folding over maneuver will cause contact of the hydratable solution-holding component with the exposed hydrating fluid. Yet another embodiment has the hydrating liquid-storage component and the hydratable solution-holding component attached to a first portion of the system while a second portion of the system contains pins for puncturing the hydrating liquid-storage component. In this embodiment, manual alignment and assembly of the first and second portions causes the pins to puncture the hydrating liquid-storage component and thereby release the fluid to hydrate the hydratable solution-holding component.

In the above-described devices, the need to manually assemble the separate system portions inhibits inadvertent hydration of the hydratable solution-holding component. Nevertheless, separate, or foldable, portions are costly and cumbersome to use. Such devices also depend on proper assembly and manipulation by the user. Mis-alignment or improper use could result in inefficient hydration.

As with the previously discussed Haak embodiments, the hydrating rate, the completeness of the fluid transfer, and the uniformity of fluid distribution in the above-described devices are also affected by the characteristics and properties of the individual components, i.e., the interposed electrical current distribution element material, the hydratable solution-holding component material, the hydrating liquid-storage component material, and the optional wicking material. The precision of the alignment of the system portions with each other will also be a factor. In addition, specifically for the device featuring puncturing pins to release the hydrating liquid, the variability in size and shape of the resultant torn or punctured openings created within the hydrating liquid-storage component material or between the hydrating liquid-storage component and the hydratable solution-holding component will affect the escape and dispensing of the hydrating liquid.

Approaches disclosed by Gyory et al. include a hydrating liquid-storage component which is separated from a hydratable solution-holding component by a liquid-impermeable sheet. Certain embodiments rely on packaging means to protect from inadvertent release of the hydrating liquid and to cause "automatic" hydration upon removal of the device from the package. The packaging means which effect "automatic" hydration include compression means to rupture or burst the liquid-impermeable sheet; blade means to puncture the liquid-impermeable sheet; and pull-tab means to rip or tear the liquid-impermeable sheet. An alternative embodiment attaches the pull-tab means, for ripping or tearing the liquid-impermeable sheet, to a release liner covering a skin contacting surface of the device. In this embodiment, removal of the release liner prior to placement on the patient "automatically" pulls the pull-tab means to rip or tear the liquid-impermeable sheet and thereby release the hydrating liquid. Like the Haak invention, Gyory also discloses liquid flow control means for directing the flow of hydrating liquid through the breached liquid-impermeable sheet to the hydratable solution-holding component.

It can be seen that, in Gyory's devices, it is the liquid-impermeable sheet separating the hydrating liquid-storage component from the hydratable solution-holding component which is physically ruptured, punctured, or ripped. The material comprising the hydrating liquid-storage component, however, remains intact. After the liquid-impermeable sheet is breached and the hydrating liquid is released, the material which formed the now-depleted hydrating liquid-storage component remains positioned within the device. In the case of a ruptured or punctured sheet, all of the now-breached liquid-impermeable sheet material also remains entirely within the device. In the pull-tab embodiment, some of the sheet material is ripped or torn away and is removed from within the device with the attached pull-tab. Nevertheless, in all cases, a substantial portion of the liquid-impermeable sheet material as well as all of the hydrating liquid-storage component material remains within the device following the hydration process.

The rupturing, puncturing, or tearing of the liquid-impermeable sheet material exposes torn edges and, thus, inner layers, of the liquid-impermeable sheet including, for example, foil edges. The hydrating liquid-storage component material and the breached liquid-impermeable sheet material, including exposed torn inner layer edges, remain within the device. These no-longer needed materials could interfere with electrical current distribution. These materials also contact the now-hydrated solution-holding component such that deleterious communication with the solution is possible. For example, over long-term iontophoresis, i.e. many hours, materials such as exposed foil edges could corrode.

It would be advantageous to be able to separate the materials associated with the hydrating liquid-storage component from the hydrated bioelectrode following the hydration process.

SUMMARY OF THE INVENTION

It is a primary object of the present invention to provide methods and apparatus permitting rapid and thorough hydration of an initially dry hydratable matrix member contained within a bioelectrode element of an iontophoretic delivery system without requiring cumbersome manipulations or assembly of separate members of the bioelectrode element. References to either a bioelectrode element or, more specifically, to a matrix member, will hereinafter be referred to as "hydratable" or "non-hydrated" when used to indicate the initial "dry" state and as "hydrated" to indicate the state following hydration.

Another object of the present invention is to provide methods and apparatus permitting thorough transfer from within a hydration assembly, contained within the hydratable bioelectrode element, of substantially all of the desired hydrating liquid into the hydratable matrix member. The hydration assembly of the present invention advantageously ensures accurate achievement of desired ion concentrations and saturation of the hydratable matrix member thus increasing the accuracy of calculated iontophoretically delivered medicament dosage.

Yet another object of the present invention is to provide methods and apparatus permitting thorough hydration of a hydratable matrix member of a bioelectrode element from a self-contained hydration assembly wherein the hydration assembly, following activation resulting in hydration of the matrix member of the bioelectrode element, is completely separable from the now-hydrated bioelectrode element. In this manner, potential problems associated with material from the spent hydration assembly remaining within the bioelectrode element, such as interference with conduction of the electrical current and deleterious interactions with the substances in solution within hydrated matrix members, are avoided.

A further object of the present invention is to provide methods and apparatus permitting a bioelectrode element to have a self-contained hydration assembly which is simple to activate yet not subject to inadvertent activation or to partial or incomplete activation.

An additional object of the present invention is to provide an integral bioelectrode element for use in an iontophoretic delivery system which can be manufactured using existing equipment and techniques and having members which can be advantageously separately manufactured for subsequent assembly into an integral unit.

These and other objects and advantages of the invention will be better understood by reference to the detailed description, or will be appreciated by the practice of the invention.

To achieve the foregoing objects, and in accordance with the invention as embodied and broadly described herein, the apparatus of the invention comprises an initially non-hydrated bioelectrode element for use in an iontophoretic delivery system. The bioelectrode element of the present invention has at least one current distribution element associated with a hydratable matrix member wherein the hydratable matrix member is hydrated through activation of a self-contained removable hydration assembly. The bioelectrode element of the present invention preferably further comprises fixation means for securing the bioelectrode element to a desired body surface and a cover membrane for protecting the hydratable matrix member.

The removable hydration assembly preferably includes an initially sealed liquid-storage component which maintains the desired hydrating liquid in isolation from the hydratable matrix member until such time as hydration is desired. The sealed liquid storage component comprises two sides each having a pocket formed therein. The sides are positioned so that the pockets define a volume therebetween to contain the desired hydrating liquid. It is preferred that the first side is substantially rigid to thereby maintain its shape during handling and use of the bioelectrode element. The second side is also preferably substantially rigid to thereby maintain its shape during handling. The pocket within the second side, however, is capable of being deformed in the direction of the first pocket in response to direct application of force on the outer surface of the second pocket. Preferably, the two pockets are sized and shaped such that progressive deformation of the second pocket toward the first pocket permits the second pocket to become inverted in a manner that results in the inverted second pocket becoming substantially fittingly aligned within the first pocket in the rigid first side. In other words, the second pocket "collapses" into the first pocket. This deforming and inverting of the second pocket into the first pocket forces the second pocket into close alignment with the inner surface of the first pocket such that the volume between the two pockets is contracted to the point of being substantially completely eliminated.

In the presently preferred embodiment, the two pockets are shaped and sized to form rounded hemispherically-shaped configurations protruding opposingly from each other such that a substantially spherical volume is described therebetween. It will be appreciated that the two pockets could be shaped in other forms which would permit a suitable volume to be formed therebetween and would be capable of collapsing one within the other to thereby substantially completely eliminate the volume. For example, although opposing rounded hemispheres are preferred, the pockets could be configured as flattened hemispheres as well.

Because the hydrating liquid is contained within the volume created between the two pockets, deforming and inverting of the second pocket generates pressure within the sealed liquid-storage component which results in unsealing of the sealed liquid-storage component. Unsealing occurs at a preselected release site. The preselected release site is positioned adjacent to the hydratable matrix member to thereby permit the hydrating liquid released from the liquid-storage component to flow into the hydratable matrix member. The preselected release site can be defined, for example, by weakening the seal between the two sides of the sealed liquid storage component in some manner at the desired release site location.

Preferably, the hydration assembly includes a mounting member for maintaining the sealed liquid-storage component adjacent to the hydratable matrix member. The mounting member preferably comprises a tray formed integrally with the substantially rigid first side of the liquid-storage component such that the first pocket in the first side protrudes from the plane of the tray. The second side of the liquid-storage component is preferably formed with an annular flange surrounding the pocket to provide an area for sealing attachment to the tray. The first pocket can be any suitable size and shape and the second pocket is sized and shaped to fittingly align within the first pocket, i.e., the second pocket is slightly smaller but corresponding in shape to the first pocket. The annular flange is sealed to the tray such that the second pocket is positioned to protrude from the plane of the tray directly opposite the protruding first pocket thereby forming a sealed volume between the two pockets.

The volume is filled with the desired quantity of the desired hydrating liquid by any suitable means known in the art. It will be appreciated that filling may be achieved before or after the second side is sealed to the tray, as desired, so long as the liquid storage component is sealed in some manner once the hydrating liquid is delivered. It will further be appreciated that the volume between the pockets may be substantially identical to the desired volume of hydrating liquid or may be in excess of the volume of hydrating liquid. If desired, an excess volume could contain air or another substance.

In addition, the rigid tray is preferably formed with a depression sized and shaped to hold the hydratable matrix member adjacent to the sealed liquid-storage component. In a preferred embodiment, a first lip, opening toward the liquid-storage component, and an adjacent second lip, opening toward the depression, are also formed in the tray. In this manner, the hydrating liquid released from the liquid-storage component at the first lip, which is contiguous with the preselected release site where unsealing occurs, is directed by the adjacent second lip into the hydratable matrix member held within the depression.

The hydration assembly comprising the tray and integral liquid-storage component is attached to the remaining components of the bioelectrode element in a removable manner. Accordingly, following hydration of the matrix member, the spent hydration assembly can be separated from the bioelectrode element to thereby prevent further interaction with the remaining components of the now-hydrated bioelectrode element.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENTS

Figure 1:
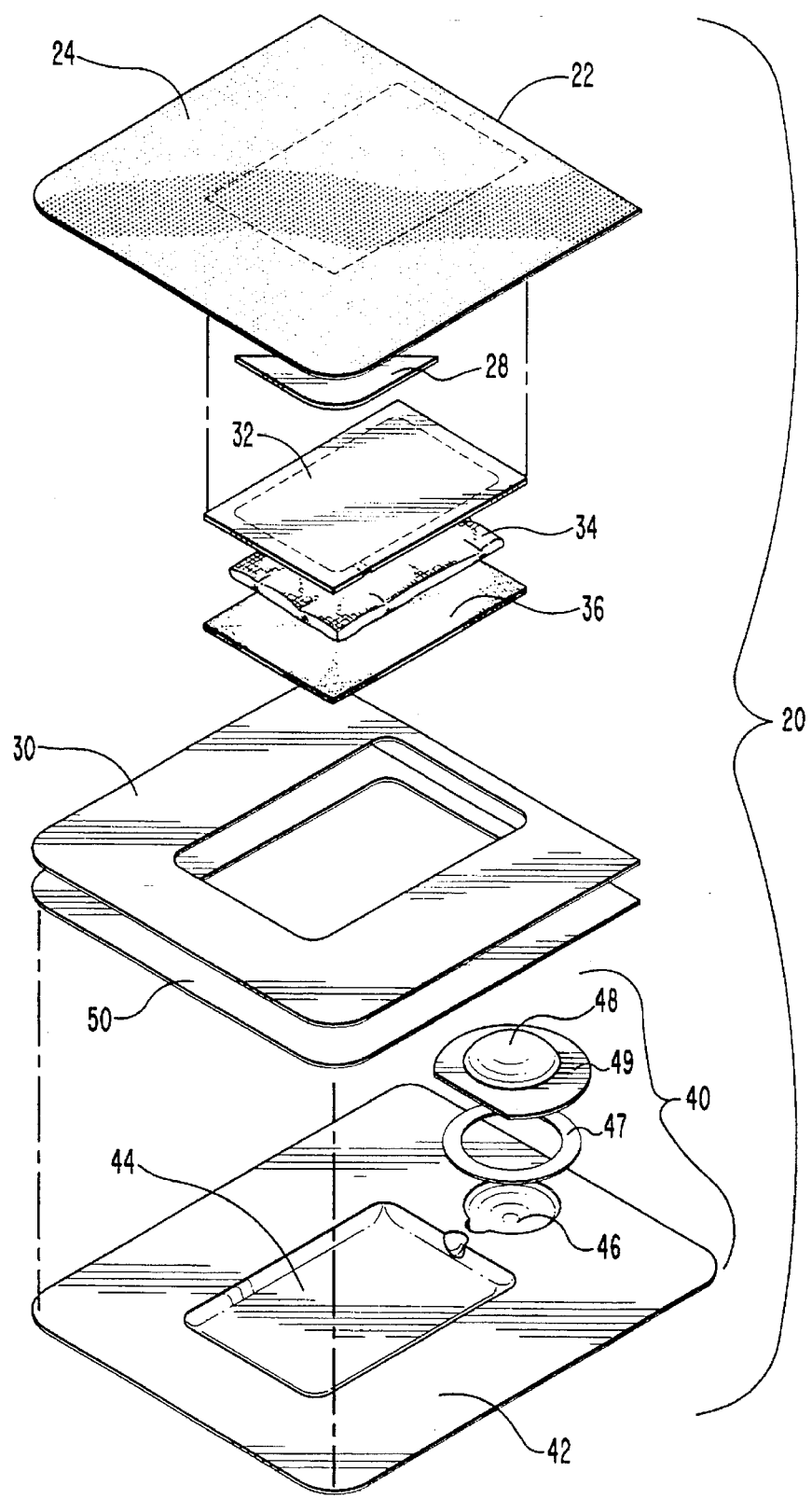
FIG. 1 is an exploded view of a preferred embodiment of a bioelectrode element constructed in accord with the present invention.

The present invention relates to iontophoretic delivery devices. Iontophoresis is recognized as a useful process for the non-invasive transdermal or transmucosal delivery of beneficial agents. An iontophoretic delivery device typically comprises at least one bioelectrode element, an electrical power source such as a disposable battery, and an electronic controller. The electrical power source and controller can be optionally positioned in either direct or remote communication with each other and with the bioelectrode element.

The bioelectrode element of an iontophoretic delivery device is placed in fluid communication with a skin or mucosal body surface. The bioelectrode element comprises at least one current distribution element and an associated reservoir of some type containing ions in solution such that application of the electrical current results in migration of the ions from the reservoir through the body surface and into the body tissue. Iontophoretic delivery of ions is typically accomplished using two current distribution elements, each current distribution element being associated with an ionic solution-containing reservoir. Typically, one reservoir is associated with the positive electrical current distribution element and the other reservoir is associated with the negative electrical current distribution element, although alternating current may also be utilized for certain applications. Also typically, one reservoir contains an ionized medicament solution and one contains a dispersive electrolyte solution, although, again, different types of solutions or combinations of solutions may be utilized for certain applications.

It can be seen that either two separate bioelectrode elements, each having one current distribution element and an associated reservoir, or a single bioelectrode element, comprising two separated current distribution elements and two associated reservoirs, can be used. The methods and apparatus of the present invention comprise an initially non-hydrated bioelectrode element for use in an iontophoretic delivery device. The bioelectrode element of the present invention is adaptable for use with various ionic chemical agents, hereinafter usually referred to as "medicaments." The teachings contained herein should be understood as having applicability to bioelectrode elements comprising only one, or more than one, current distribution element and associated reservoir.

A feature of the bioelectrode element of the present invention is that the bioelectrode element is initially in a non-hydrated state to thereby avoid problems associated with the manufacture, storage, handling, stability, and use of pre-hydrated bioelectrode elements. Another feature of the present invention is provision of self-contained means for hydrating an associated hydratable matrix member, which hydrated matrix member will serve as a medicament or electrolyte solution reservoir during iontophoresis. The hydrating means includes a removable hydration assembly containing an initially sealed liquid-storage component which isolates a pre-determined quantity of hydrating liquid from the hydratable matrix member until such time as hydration is desired.

In addition to being simple to use, an advantage of the present invention is that the self-contained hydrating means is resistant to inadvertent activation. Yet, when desired, user activation of the self-contained hydrating means results in rapid and thorough transfer of the desired hydrating liquid into the hydratable matrix member.

As mentioned, initially, the matrix member is non-hydrated such that the bioelectrode element can be stably stored and handled. The non-hydrated, i.e., dry, matrix member is referred to as "hydratable" because it must be hydrated prior to use. Hydration is accomplished by means of a removable hydration assembly containing the desired hydrating liquid. Thus, the dry matrix member may contain a dry form of the desired medicament or electrolyte solution which is hydrated with an appropriate diluent or the dry matrix member may contain only support material which is hydrated with the appropriate medicament or electrolyte solution. It may also be possible to store and handle combinations of medicaments wherein some are stable in dry form and some are stable in hydrated form but the combination is not stable and must be kept separated prior to use.

In such circumstances, the stable dry medicaments can be stored in the dry matrix member and the stable hydrated medicaments can be stored in the hydrating liquid-storage component until the desired time of use.

Also integral to the presently preferred bioelectrode element of the present invention is a predetermined amount of hydrating liquid for each hydratable matrix member which is initially maintained in isolation from the hydratable matrix member. The present invention features an integral removable hydration assembly providing means for storing the hydrating liquid and dispensing the hydrating liquid into the hydratable matrix element in a rapid and thorough manner at the time of desired use. The hydration assembly is initially integral with the bioelectrode element of the present invention and comprises a predetermined amount of hydrating liquid isolated from the hydratable matrix member and stored within a sealed liquid-storage component. Following activation of the hydration assembly and completion of the hydration process, the entire hydration assembly is separable from the remaining components of the now-hydrated and ready-to-use bioelectrode element.

The bioelectrode element of the present invention has at least one current distribution element associated with a hydratable matrix member wherein the hydratable matrix member is hydrated through activation of a self-contained removable hydration assembly. It should be understood that a bioelectrode element in accord with the present invention could comprise two hydratable matrix members each having an associated removable hydration assembly and each being associated with a respective electrical current distribution element.

The bioelectrode element of the present invention preferably further comprises fixation means for securing the bioelectrode element to a desired body surface and a cover membrane for protecting the hydratable matrix member from the outside environment. The removable hydration assembly preferably includes an initially sealed liquid-storage component which maintains the desired hydrating liquid in isolation from the hydratable matrix member until such time as hydration is desired.

FIG. 1 illustrates an exploded view of the components of a preferred embodiment of a bioelectrode element 20 constructed in accordance with the present invention. The bioelectrode element of the present invention contains at least one current distribution element 32, an associated hydratable matrix member 34, and self-contained means for hydrating the matrix member such as hydration assembly 40.

The bioelectrode element 20 of the present invention is preferably a compact, lightweight, and largely disposable integral unit. It will be understood by those of skill in the art that, although the bioelectrode element is illustrated as having only one current distribution element and associated hydratable matrix member, a bioelectrode element in accord with the present invention could, alternatively, comprise two current distribution elements maintained in close proximity to, but separate from, each other.

The bioelectrode element 20 of the present invention preferably comprises a chassis member 22 for supporting its various component parts. Preferably, chassis member 22 is flexible to facilitate attachment of the bioelectrode element to a body surface. Chassis member 22 comprises an exterior, non-conducting, liquid-impermeable surface 24 and an interior non-conducting adhesive surface 26 (shown in FIG. 3). As shown in FIG. 1, a current distribution element 32 is preferably sized and shaped such that, when attached in a substantially central position to interior adhesive surface 26 (shown in FIG. 3), portions of the adhesive surface extend on all sides of the current distribution element. These portions of the adhesive surface are available for contacting the body surface and, thus, should be of sufficient size to securely hold the bioelectrode element in place. The body-contacting portions of the adhesive surface are preferably covered with a release liner 30 of the strippable type known in the art to permit easy separation, i.e., stripping, of the interior adhesive surface from the release liner. The interior adhesive surface 26 preferably has a non-adhesive tab portion 28 (best shown in FIG. 3) to permit grasping by a user and thereby facilitate easy stripping of the interior adhesive surface from the release liner.

The current distribution element 32 is preferably formed by depositing a conductive material onto a suitable backing thereby forming an electrode layer. For example, the electrical current distribution elements may be formed of a metal foil, conductive carbon, or metal deposited or painted on a suitable backing. Examples of suitable materials include silver, zinc, silver/silver chloride, aluminum, platinum, stainless steel, gold, conductive carbon compounds and titanium. Alternatively, the electrical current distribution element layer could be formed of a conductive filler supported by a polymer matrix. The active surface area for the electrical current distribution element should preferably correspond to the surface area of the associated hydratable matrix member 34 and should preferably comprise a surface area of about 8 $cm^2$.

The current distribution element has one side secured to the interior surface of chassis member 22 and one side contacting the hydratable matrix member 34 which is sized and shaped to substantially correspond to the size and shape of the current distribution element. Hydratable matrix member 34 is designed to provide a suitable support matrix for either a dry form of medicament or a dry form of a dispersive electrolyte. When hydrated, the volume of the matrix member is preferably less than one milliliter of drug or electrolyte fluid. Preferably, the hydratable matrix element comprises a support material suitable for impregnation with the desired medicament. Suitable support materials would include, for example, a polyurethane sponge such as FOAMEX felted Z-90 firmness 2 polyurethane foam or FOAMEX ACQUELL hydrophilic foam manufactured by Foamex Foam Inc.; a nonwoven polyester such as a spunbonded polyester manufactured by REEMAY, a member of The InterTech Group, Inc. located in Old Hickory, Tenn.; or a fiber or cloth material.

It is generally desirable to load the hydratable matrix member with a hydrophilic thickener such as a high molecular weight polyethylene oxide (PEO), such as POLYOX NF coagulant grade made by Union Carbide. Alternative hydrophilic materials include high molecular weight polyvinyl alcohol (PVA), poly-N-vinyl pyrrolidone (PVP), or other substituted pyrrolidones, polyacrylamide (PAAm), poly-N-isopropyl acrylamide (NIPPAm), polyhydroxyethyl methacrylate (PHEMA), or hydrophilic substituted HEMAs, polysaccharides such as agarose, hydroxyethyl cellulose (HEC), hydroxypropylmethyl cellulose (HPMC), hydroxypropyl cellulose (HPC), carboxymethyl cellulose (CMC), dextrans, modified starches, modified collagens, xanthan gum, guar gum, modified natural gums, partially neutralized polyelectrolytes such as polyacrylic acid, polyimides, and alginates. In some circumstances, copolymer mixtures of the foregoing may also be suitable. The preferred polymers, however, are non-ionic or non-electrolyte hydrophilic polymers such as PEO, PVP, PAAm, HPC and HEC, or copolymers of these, because these materials do not contain large numbers of ionizable moieties which would compete as charge carriers with the drug to be iontophoretically administered. Commercial forms of HPC are preferred such as KLUCEL HF NF. The polymer is chosen so that fully dissolved thickener is viscous enough to remain within the hydrated matrix. For example, with the preferred KLUCEL HF NF, a concentration between 1 and 1.5% in the hydrated matrix has sufficient viscosity.

It may also be desirable to include various agents such as solvents, surfactants, wetting agents, or other excipients in the solution. A surfactant has been found particularly useful to assist in rapid hydration of the hydratable matrix member. Hence, it has been found useful to add TWEEN 20 nonionic polysorbate-fatty acid ester surfactant (available from ICI America) to the hydratable matrix member composition. The addition of a surfactant such as TWEEN 20 has been found to aid the rate of wetting during hydration. Although for purposes of brevity the following discussion is primarily directed to the use of TWEEN 20, it should be understood that other surfactants could also be used in place of TWEEN 20 in those situations where a surfactant is desired. Examples of other useful surfactants are NEODOL 91-6 (a nonionic primary alcohol ethoxylate manufactured by Shell Chemical Co.); TERGITOL 15-S-7 (a nonionic secondary alcohol ethoxylate manufactured by Union Carbide); PLURONIC POLOXAMER F68 or F127 made by BASF; and (poly(ethylene oxide)/poly(propylene oxide) block co-polymer DUPONOL C or DUPONOL XL (anionic sodium lauryl sulfates manufactured by Dupont Chemical Corp.). It is desirable that the surfactant be substantially nonionic, although small quantities of ionic moieties can be permitted.

In a presently preferred embodiment of hydratable matrix member, the thickener KLUCEL HF, manufactured by Aqualon Company, 1313 No. Market Street, Wilmington, Del., and the surfactant TWEEN-20 are impregnated into a spin-laced rayon/polyester material, SONATRA 8423, manufactured by E.I. DuPont De Nemours & Co., Textile Fibers Dept., Wilmington, Del. In dry form, this composition contains 15% KLUCEL and 15% TWEEN 20 by weight. Hydration of 8 $cm^2$ of this composition with 0.5 ml water forms a solution within the SONATRA 8423 which is about 1.5% KLUCEL and 1.5% TWEEN by weight.

Also shown in FIG. 1 is an optional porous cover membrane 36 which preferably encloses the outward surface of the hydratable matrix member 34 through which ion transfer into the body surface occurs, i.e., the surface providing fluid communication between the hydratable matrix member and the body surface. Cover membrane 36 is preferably sized and shaped slightly larger than hydratable matrix member such that the cover membrane may be affixed to the interior adhesive surface and thereby maintain the hydratable matrix member in secure alignment with the current distribution element. In the absence of optional cover membrane, it should be understood that the hydratable matrix member must be secured in proper alignment with the current distribution element in some other manner.

It will be appreciated that, if a cover membrane is used, the hydrated matrix member will not directly contact the body surface but will contact the porous cover membrane which contacts the body surface. Thus, the cover membrane must be made of material which permits flux of ions therethrough. In addition, the cover membrane must be made of material which permits mass flow of hydrating liquid into the hydratable matrix member during the hydration process but preferably also provides some resistance to leakage of the ionic solution from within the matrix following hydration. Thus, the cover membrane should be made of material which has a reasonable mass flow rate for the hydrating liquid and preferably has a lesser flow rate for the ionic solution formed within the matrix member upon hydration.

Following hydration of the hydratable matrix member and separation of the hydration assembly from the bioelectrode element, the porous cover membrane protects the surface of the hydrated matrix member from damage or leakage by providing a tough, abrasion- and tear-resistant surface. Accordingly, suitable materials for the cover membrane preferably have the following properties: reasonable mass flow rate for the hydrating liquid, flexibility, hydrophilicity, inertness, and toughness. Practical choices include expanded and supported acrylic, polysulfone, PVDF, poly(vinylidene fluoride), PTFE, (polytetrafluorethylene) PP polypropylene or nylon membranes treated to be hydrophilic. Alternatively, a thin mesh or weave comprised of any of the above-identified polymers or of polyester could be used. The presently-preferred material for the cover membrane is VERSAPOR 10000 which comprises an expanded acrylic with fibrous nylon support having pores of 10 microns. VERSAPOR 10000 is available from Gelman Sciences, Membrane and Device Division, 600 South Wagner Road, Ann Arbor, Mich.

As shown in FIG. 1, a presently preferred hydration assembly 40 comprises a mounting tray 42 having a depression 44 formed therein sized and shaped to substantially closely accommodate the cover membrane 36, the hydratable matrix member 34, and the current distribution element 32 which are mounted in consecutive alignment on chassis member 22. A portion of the mounting tray surrounding the depression is preferably sized and shaped to provide a surface for reversibly attaching the tray 42 to release liner 30 and thereby to chassis member 22. Reversible attachment of tray 42 to release liner 30 can be accomplished by conventional methods such as a double-sided adhesive layer 50 as illustrated. In this manner, following hydration of the hydratable matrix member, the release liner permits separation of the entire hydration assembly and attached release liner from the remaining components of the bioelectrode element. Those remaining components, the porous cover membrane, the now-hydrated matrix member, the current distribution element, and the chassis member can then be secured to a body surface for use. Thus, the spent hydration assembly can be removed and discarded, if desired, to thereby prevent further interaction with the now-hydrated bioelectrode element.

Another portion of the tray 42 adjacent to the depression 44 is formed to comprise a first pocket 46 in a first side of a liquid-storage component. The first pocket 46 is preferably a substantially rigid hemispherically-shaped protrusion formed in tray 42. A second pocket 48 is provided in a second side of the liquid-storage component. The second pocket is sized and shaped to substantially correspond to the size and shape of the first pocket, i.e., preferably a slightly smaller hemispherical configuration, such that the second pocket can become fittingly aligned within the first pocket when deformed by an applied pressure as described below. It will be appreciated that other shapes may be used in place of hemispherically-shaped pockets. For example, pockets having a flattened hemisphere shape will perform the function of describing a volume for containing the hydrating liquid therebetween and being capable of collapsing one within the other as described below.

The second side of the liquid-storage component also has an attachment portion permitting the second side to be affixed to tray 42. The attachment portion is preferably an annular flange 49 surrounding the second pocket 48 as shown. Annular flange 49 may be attached to the tray in any conventional manner such as heat welding or adhesive bonding. Preferably, as shown, a double-sided adhesive layer 47 can be used to sealingly engage the second side to the tray in a position such that the second pocket 48 of the second side protrudes from the plane of the tray directly opposite the protruding first pocket 46 to thereby describe a substantially spherical sealed volume to contain the desired hydrating liquid between the first and second pockets. As noted above, the pockets may be shaped in other configurations such that the sealed volume need not be substantially spherical.

Figure 2:
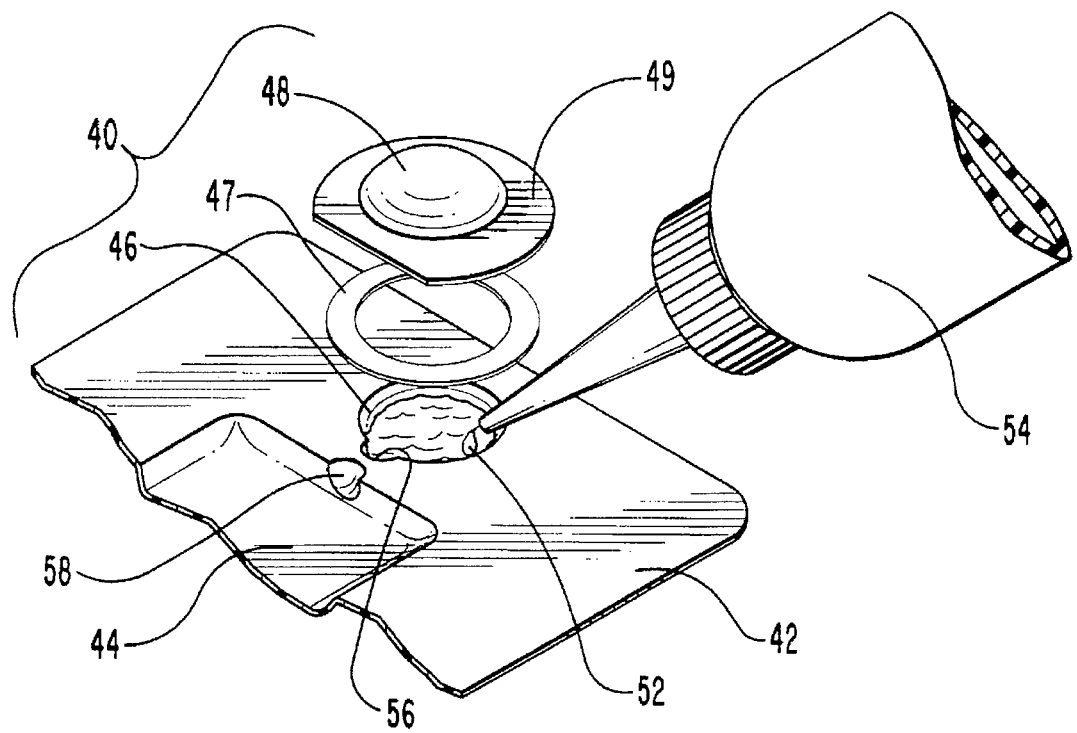
FIG. 2 is an exploded view of a hydration assembly of the preferred embodiment of FIG. 1.

FIG. 2 illustrates an exploded view of a hydration assembly in accord with the present invention. The volume between the pockets 46 and 48 is to be filled with the desired quantity of the desired hydrating liquid and sealed. Filling of the volume can be achieved by any suitable means, as schematically illustrated in FIG. 2 through use of a dropper 54. FIG. 2 illustrates the desired quantity of hydrating liquid 52 being delivered into the first pocket 46 of the liquid-storage component. The annular flange 49 attachment portion of the second side can then be sealingly affixed to tray 42 to thereby form the sealed liquid-storage component. The depiction of FIG. 2 is illustrative only and it will be appreciated that the second side may be affixed to the tray before the hydrating liquid is delivered into the volume created between pockets 46 and 48, if desired, provided that the liquid storage component is sealed once the hydrating liquid is delivered. It will further be appreciated that the volume between the pockets may be substantially identical to the desired volume of hydrating liquid or may be in excess of the volume of hydrating liquid. If desired, an excess volume could contain air or another substance.

It has been assumed in the foregoing discussion that medicament is stored in dry form as a component of the hydratable matrix element. It should be appreciated that medicament may alternatively be stored in hydrated form within the hydrating liquid-storage member. Another alternative would be to store one or more forms of medicaments in both the dry hydratable matrix element and within the hydrating liquid. Such a configuration may be particularly useful with multiple medicaments that may cross-react with each other or otherwise deteriorate during storage or to increase concentrations of medicament obtained at the time of use.

As described above, following placement of the desired quantity of the desired hydrating liquid into the first side 46, and attachment of annular flange 49 to tray 42 such that the second pocket 48 protrudes from the plane of the tray directly opposite the protruding first pocket 46, a sealed liquid-storage component is formed between the two pockets. The sealed liquid-storage component is integral with tray 42 and, when the tray is attached to the remaining components of the bioelectrode element, the sealed liquid-storage component will be adjacent to the hydratable matrix member positioned within the depression 44 formed within tray 42.

From the foregoing, it will be understood that the sealed liquid-storage component preferably comprises two sides each having a pocket positioned to define a volume therebetween to contain the desired hydrating liquid. The first side is preferably substantially rigid to thereby maintain its shape during handling and use of the bioelectrode element. The second side is also preferably substantially rigid to thereby maintain its shape during handling, yet, at the same time, the pocket in the second side must be capable of being deformed in the direction of the first pocket in response to a moderate force such as would be applied by a user's finger. Preferably, the two pockets are sized and shaped such that progressive deformation of the second pocket toward the first pocket permits the second pocket to become inverted in a manner that results in the inverted second pocket becoming substantially fittingly aligned within the first pocket in the more rigid first side. In other words, the second pocket "collapses" into the first pocket. This deforming and inverting of the second pocket into the first pocket forces the second pocket of the sealed liquid storage component into close alignment within the first pocket such that the volume between the two pockets is contracted to the point of being substantially completely eliminated.

It will be appreciated from the above description that the hemispherically shaped pockets of the first and second sides of the sealed liquid storage component are arranged to protrude in opposite directions from the plane of tray 42 such that the second pocket 48 may be inverted and collapsed within the first pocket 46. The material for the collapsible second pocket should be thin enough to permit deformation and inversion to the collapsed position with a moderate amount of force yet be of sufficient rigidity to resist inadvertent deformation during normal shipping and handling. A sufficient force to deform, invert, and collapse the second pocket is preferably the force generated by pressing upon the protruding pocket with a thumb or finger or by squeezing the protruding first and second pockets between a thumb and forefinger. Although the material needs to be thin enough to permit deformation, it will preferably be thick enough to ensure uniform and rapid collapse. In other words, the second pocket preferably has a thickness that prevents any area from tending to collapse preferentially which could result in an incomplete collapse and incomplete liquid release. A material of adequate thickness will allow the entire pocket surface to collapse uniformly and all at once, i.e., substantially instantaneously, into the inverted position upon application of a force that exceeds the collapse-pressure threshold of the material. Typically, the rapid collapse results in a "pop" as the second pocket collapses into the first pocket in the first side and ensures that the liquid is released in a manner that propels substantially all of the hydrating liquid through the release site. In this manner, the force of the expulsion of the liquid helps ensure that the hydrating liquid rapidly and thoroughly hydrates the hydratable matrix member.

Tray 42 and the integrally formed first side 46 are preferably formed of a material which is substantially rigid. The material for the first side typically can be thicker than the material for the second side. It is important that the first side be configured to have sufficient depth such that the inverted pocket of the second side cannot "rebound" out of the inverted position when the applied force is removed. To ensure the preferred rapid collapse occurs, it is important that the depth, diameter, and material thickness for both the first side and the second side of the liquid storage component are carefully selected and scaled proportionately to the overall size of the liquid-storage component. For example, the following dimensions yield a liquid storage component which functions in the preferred manner: second pocket diameter, 13.5 mm, second pocket depth, 2.0 mm, second pocket thickness, 7 mil (0.005 inch); first pocket diameter, 14.7 mm, first pocket depth, 1.8 mm, and first pocket thickness, 12 mil (0.012 inch).

Material for both the first and second side of the liquid storage component must protect the hydrating liquid from evaporation over the desired product shelf life. Because moisture vapor diffusion decreases with increasing material thickness, the first side material may naturally provide a sufficient moisture barrier. It is possible to add a moisture vapor transmission rate (MVTR) barrier coating or laminate such as a foil layer or a PVDC (poly(vinylidene chloride)) polymer coat to a material with otherwise insufficient moisture barrier properties. In addition, the selected material for the first and second side of the liquid storage component, or at least the interior surface material, must be stable during long-term exposure to wetness from the contained hydrating liquid. The material may be either transparent or opaque. It is preferred that the second side be formed of transparent material to permit viewing of the contents of the liquid storage component and because such material has better collapsibility than, for example, foil material. Finally, the selected material for either side must be formable, either by heat or pressure, or both, to create a shaped pocket from the flat material.

Examples of suitable commercially available transparent materials for forming the rigid first side of the liquid storage component include the following: ALPET-T multilaminate transparent packaging film, a PETG/PE/PVDC (poly(ethylene terephthalate) glycol/polyethylene/poly(vinylidene chloride)) 13 mil composite (Klockner-Pentaplast of America, Inc., Klockner Road, P.O. Box 500, Gordonsville, Va. 22942); MIRREX 1025, 10–15 mil or MIRREX 3002, 10–15 mil, both are clear pharmaceutical blister packaging and laminating films, MIRREX 3007, 10–15 mil, a clear laminated FDA grade medical packaging film (American Mirrex Corp., 1389 School House Road, P.O. Box 708, New Castle, Del.). 19720; KODAR PETG copolyester 6763, extruded into 12–15 mil film (Eastman Chemical Products, Inc., Plastics Division, Kingsport, Tenn. 37662). An example of a commercially available opaque material is Product TL11 and TL12, double-layered together, a plastic/thick foil laminated film product available from Robert Victor Neher Ltd., Aluminium Foil Rolling and Converting Mills, Finkernstrasse 30, CH-8280 Kreuzlingen, Suisse.

Examples of suitable commercially available transparent materials for forming the second side of the liquid storage component include the following: MIRREX 1025, 7 mil or MIRREX 3002, 7 mil, both are clear pharmaceutical blister packaging and laminating films, MIRREX 3007, 7 mil, a clear laminated FDA grade medical packaging film, products of American Mirrex Corp., 1389 School House Road, P.O. Box 708, New Castle, Del. 19720; Product #8B35-112 Velvet LEXAN 5 mil film, a clear polycarbonate film manufactured by General Electric Sheet Products, Inc. and distributed by Commercial Plastics Supply Corp., 475 West 3600 South, Salt Lake City, Utah 84115; and Product #0.005 454., a polyester 5 mil film manufactured by ICI Melinex and distributed by Spectra Symbol, 3101 West 2100 South, Salt Lake City, Utah 84119.

Because the hydrating liquid is contained within the volume between the pockets in each of the two sides of the sealed liquid-storage component, deforming and inverting of the second pocket into the first pocket generates pressure within the sealed liquid-storage component which results in unsealing at a preselected release site. The preselected release site is positioned adjacent to the hydratable matrix member to thereby permit the hydrating liquid released from the liquid-storage component to flow into the tray and into the hydratable matrix member positioned therein. The preselected release site can be defined, for example, by weakening the seal between the two sides in some manner at the desired release site location.

As illustrated in FIG. 2, in a preferred embodiment, a preselected release site is defined by a first lip 56 formed in tray 42 such that lip 56 opens toward the sealed liquid-storage component. Accordingly, as the pocket 48 in the second side of the sealed liquid-storage component is progressively deformed and inverted into the first pocket 46, more and more of the hydrating liquid is forced into the lip until eventually the seal breaks and the liquid is released at the lip location. Preferably, as shown in FIG. 2, a second lip 58 is also formed in tray 42 in a position adjacent to first lip 56 and opening onto the depression 44 such that liquid flowing through the first lip into the second lip is directed into the hydratable matrix member held within the depression.

Figure 3:
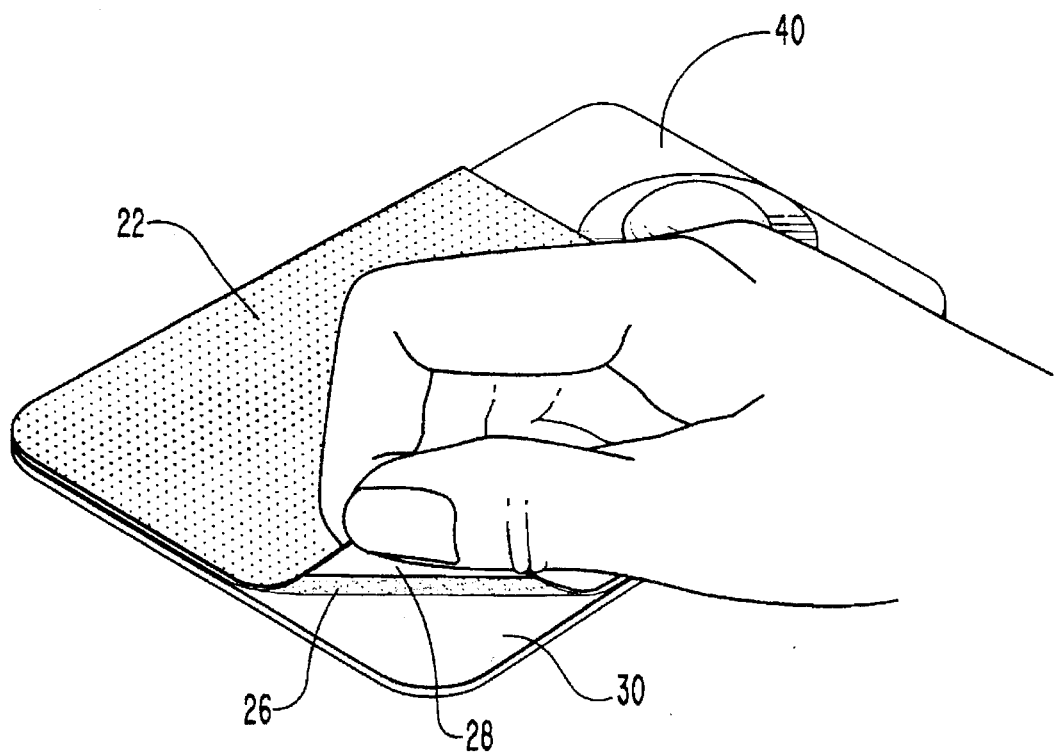
FIG. 3 is a perspective view of the preferred embodiment of FIG. 1.

FIG. 3 illustrates a preferred embodiment of a bioelectrode element in accord with the present invention in the initial non-hydrated state. From the foregoing, it should be understood that progressive deforming and inverting of the second pocket in the direction of the first pocket in the first side of the sealed liquid-storage component is easily initiated by application of direct force by a user desiring to hydrate the bioelectrode element. Preferably, the force is continuously applied until such time as the collapse-pressure threshold of the second pocket material is exceeded and the second pocket uniformly and rapidly collapses into the pocket in the first side. At this point, the volume between the two pockets is essentially eliminated forcing substantially all of the hydrating liquid to be propelled through the first lip, into and through the second lip, and into the tray depression. From the tray, the liquid flows rapidly through the cover membrane and into the hydratable matrix member such that thorough hydration is achieved. Thus, the hydration process is completed easily and rapidly.

As illustrated in FIG. 3, following hydration of the bioelectrode, tab member 28 can easily be grasped and pulled to thereby begin separating the interior adhesive surface 26 from the release liner 30. The chassis member 22 is thereby separated from the hydration assembly 40. In this manner, the spent hydration assembly is completely removed from association with the hydrated bioelectrode element comprising the chassis member with attached current distribution element, hydrated matrix member and porous cover membrane (see FIG. 1). The hydrated bioelectrode element is ready to be affixed at a desired location on a body surface such that iontophoretic delivery of ions therethrough can occur.

The present invention may be embodied or utilized in other specific forms or manners without departing from its spirit or essential characteristics. The described embodiments and methods are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hydratable bioelectrode element for use in an iontophoretic delivery device comprising:
    an electrical current distribution element;
    a hydratable matrix member in electrical communication with the electrical current distribution element;
    hydration means positioned to fluidly communicate with the hydratable matrix member for hydrating said matrix member, said hydration means including a hydration assembly comprising:
        a hydrating liquid stored within a volume between a first pocket in a first side and a second pocket in a second side of a sealed liquid-storage component;
        at least one of said first and second pockets of said sealed liquid-storage component being a collapsible pocket, the other pocket being more rigid than said collapsible pocket to thereby maintain its shape during use, such that said collapsible pocket collapses into an intact inverted position substantially fittingly aligned within the other pocket in response to an applied force to thereby substantially eliminate said volume between said first pocket and said second pocket; and
        a selected release site between said first side and said second side of said sealed liquid storage component, said selected release site adapted to become unsealed and to release said hydrating liquid therethrough in response to said applied force.

2. A hydratable bioelectrode element as defined in claim 1 further comprising a chassis member having an exterior surface and an interior surface, said interior surface being secured to the electrical current distribution element.

3. A hydratable bioelectrode element as defined in claim 2 wherein the exterior surface of the chassis member comprises an electrically non-conducting liquid-impermeable layer.

4. A hydratable bioelectrode element as defined in claim 3 further comprising fixation means to secure the bioelectrode element in a desired position on a patient's body surface.

5. A hydratable bioelectrode element as defined in claim 4 wherein the fixation means comprises an adhesive layer applied to the interior surface of the chassis member.

6. A hydratable bioelectrode element as defined in claim 5 wherein the hydratable matrix member has an inward surface to provide fluid communication with the electrical current distribution element and an outward surface to provide fluid communication with a desired body surface.

7. A hydratable bioelectrode element as defined in claim 6 further comprising a porous cover membrane secured to the interior surface of the chassis member and positioned to enclose the outward surface of the hydratable matrix member and thereby secure the hydratable matrix element between the porous cover membrane and the electrical current distribution element.

8. A hydratable bioelectrode element as defined in claim 7 wherein the hydration assembly further comprises a mounting tray integral with the sealed liquid-storage component.

9. A hydratable bioelectrode element as defined in claim 8 wherein the mounting tray is formed of a substantially rigid material.

10. A hydratable bioelectrode element as defined in claim 9 wherein the mounting tray is formed integrally with said first side of said sealed liquid-storage component.

11. A hydratable bioelectrode element as defined in claim 10 wherein said first pocket in said first side is shaped as a half-sphere protruding from the plane of the mounting tray.

12. A hydratable bioelectrode element as defined in claim 11 wherein said second pocket in said second side of said sealed liquid-storage component is shaped as a half-sphere having a size to permit substantial alignment of said second pocket within said first pocket.

13. A hydratable bioelectrode element as defined in claim 12 wherein said second side further comprises an attachment portion permitting said second side to be sealingly affixed to the mounting tray such that the second pocket protrudes from the plane of the mounting tray directly opposite the protruding first pocket to thereby form the volume for containing the hydrating liquid between the first and second pockets.

14. A hydratable bioelectrode element as defined in claim 13 wherein said second pocket has a thickness that permits the entire pocket surface to collapse uniformly and rapidly into the first pocket upon application of a force that exceeds the collapse-pressure threshold of the second pocket material.

15. A hydratable bioelectrode element as defined in claim 14 wherein the mounting tray further comprises a depression for positioning therein the hydratable matrix member.

16. A hydratable bioelectrode element as defined in claim 15 wherein the mounting tray further comprises means for directing liquid released from the sealed liquid-storage component into the hydratable matrix member.

17. A hydratable bioelectrode element as defined in claim 16 wherein said directing means comprises one lip formed in a position abutting the release site of the sealed liquid-storage component and a second lip, adjacent to the first lip, formed in a position abutting the depression holding the hydratable matrix member.

18. A hydratable bioelectrode element as defined in claim 17 wherein the mounting tray is reversibly attached to the bioelectrode element such that, following hydration of the hydratable matrix member, the mounting tray is detachable to thereby permit the hydration assembly to be completely separated from the remaining components of the hydrated bioelectrode element.

19. A hydratable bioelectrode element as defined in claim 18 wherein the mounting tray further comprises an attachment surface portion surrounding said depression.

20. A hydratable bioelectrode element as defined in claim 19 further comprising a release liner having a first surface secured to said attachment surface portion of said mounting tray and a second surface secured to the interior surface of the chassis member.

21. A hydratable bioelectrode element as defined in claim 20 further comprising a tab member formed on the adhesive layer on the interior surface of the chassis member to thereby permit grasping and facilitate separation of the chassis member from the release liner.

22. A hydration assembly for use in hydrating a hydratable matrix element of a bioelectrode element, said hydration assembly comprising:

a hydrating liquid stored within a volume between a first pocket in a first side and a second pocket in a second side of a sealed liquid-storage component;

at least one of said first and second pockets of said sealed liquid-storage component being a collapsible pocket, the other pocket being more rigid than said collapsible pocket to thereby maintain its shape during use, such that said collapsible pocket collapses into an intact inverted position substantially fittingly aligned within the other pocket in response to an applied force to thereby substantially eliminate said volume between said first pocket and said second pocket;

selected release site between said first side and said second side of said sealed liquid storage component, said selected release site adapted to become unsealed and to release said hydrating liquid therethrough in response to said applied force;

a mounting tray formed integrally with said first side of said sealed liquid-storage component, said mounting tray comprising a depression for positioning said hydratable matrix member therein; and said second side of said sealed liquid-storage component comprising an attachment portion permitting said second side to be sealingly affixed to the mounting tray.

23. A hydration assembly as defined in claim 22 wherein the mounting tray is formed of a substantially rigid material.

24. A hydration assembly as defined in claim 23 wherein said first pocket in said first side is shaped as a half-sphere protruding from the plane of the mounting tray.

25. A hydration assembly as defined in claim 24 wherein said second pocket in said second side of said sealed liquid-storage component is shaped as a half-sphere protruding from the plane of the mounting tray directly opposite the protruding first pocket, said second side having a size to permit substantial alignment of said second side within said first pocket.

26. A hydration assembly as defined in claim 25 wherein said second pocket has a thickness that permits the entire pocket surface to collapse uniformly and rapidly into the first pocket upon application of a force that exceeds the collapse-pressure threshold of the second pocket material.

27. A hydration assembly as defined in claim 26 wherein the mounting tray further comprises means for directing liquid released from the sealed liquid-storage component into the hydratable matrix member.

28. A hydration assembly as defined in claim 27 wherein said directing means comprises one lip formed in a position abutting the release site of the sealed liquid-storage component and a second lip, adjacent to the first lip, formed in a position abutting the depression holding the hydratable matrix member.

29. A method for hydrating a hydratable matrix element of an iontophoresis bioelectrode, said method comprising the steps of:

providing an iontophoresis bioelectrode having an integral hydration assembly positioned to fluidly communicate with a hydratable matrix element, said hydration assembly comprising a hydrating liquid stored within a volume between a first pocket in a first side and a second pocket in a second side of a sealed liquid-storage component, said liquid-storage component having a release site adapted to become unsealed and release the stored hydrating liquid therethrough in response to an increase in fluid pressure within the sealed liquid-storage component, at least one of said pockets of said sealed liquid-storage component being progressively deformable, while remaining intact, in the direction of the other pocket in response to an applied force, said deformable pocket being sized and shaped so as to substantially fittingly align within said other pocket;

positioning the hydration assembly adjacent the hydratable matrix element;

applying progressive force to said deformable pocket of said sealed liquid-storage component such that said pocket deforms in the direction of said other pocket without loss of integrity thereby increasing the fluid pressure within said sealed liquid-storage component and unsealing said release site; and applying additional force until the deformable pocket is fittingly aligned within the other pocket to thereby effect contraction of the volume between the two pockets and force substantially all of the hydrating liquid through said release site such that said hydrating liquid flows through said release site and into said hydratable matrix member.

* * * * *